United States Patent [19]

Russo

[11] Patent Number: 5,665,376
[45] Date of Patent: Sep. 9, 1997

[54] METHOD FOR REDUCING EXCESSIVE STOMACH ACID

[76] Inventor: Ubaldo Russo, Via Boccacia 19, Bovino, Foggia, Italy

[21] Appl. No.: 552,254

[22] Filed: Nov. 2, 1995

Related U.S. Application Data

[63] Continuation-in-part of Ser. No. 194,036, Feb. 9, 1994, abandoned.

[51] Int. Cl.$^6$ ............................. A61K 9/16; A61K 9/26
[52] U.S. Cl. ..................... 424/440; 424/439; 424/441; 424/634
[58] Field of Search ........................... 424/439, 440, 424/441; 426/634

[56] References Cited

U.S. PATENT DOCUMENTS

| | | | |
|---|---|---|---|
| 2,627,462 | 2/1953 | Pettibone | 426/634 |
| 4,425,332 | 1/1984 | James | 424/440 |
| 4,950,140 | 8/1990 | Pflaumer | 424/439 |

FOREIGN PATENT DOCUMENTS

| | | | |
|---|---|---|---|
| 1087027 | 10/1984 | Canada | 426/634 |
| 2634265 | 2/1977 | Germany | 426/634 |

*Primary Examiner*—Thurman K. Page
*Assistant Examiner*—Diedra Faulkner
*Attorney, Agent, or Firm*—Patrick J. Pinto

[57] ABSTRACT

A method for treating or reducing excess stomach acidity by ingesting a predetermined dose of a flour or meal made from dried fava beans. The predetermined dose may be incorporated into edible food products such as a chewable wafer, cookie, biscuit, drink mix etc. The minimum recommended dose is at least 1000 mg. The treatment of the present invention may be taken in anticipation of excess stomach acidity or after its occurrence.

5 Claims, No Drawings

METHOD FOR REDUCING EXCESSIVE STOMACH ACID

This is a continuation in part application of my co-pending application Ser. No. 08/194,036, that was filed on Feb. 9, 1994 and is now abandoned.

BACKGROUND OF THE INVENTION

1. Field of the Invention

With regard to the classification of art, this invention is believed to be found in the general class entitled Drug, Bio-affecting and Body Treating Compositions and more particularly to those subclasses pertaining to methods for treating excessive stomach acidity.

2. Description of Related Art

For someone who suffers from "stomach acidity", it is common to use products that are commonly called antacids. These common antacids are generally sold to the user as over the counter aids. These over the counter antacids usually include chemical compositions such as; aluminum hydroxide; magnesium hydroxide; calcium carbonate; bicarbonate of soda and the like. It is known that these chemical compositions have been effective in neutralizing excess hydrochloric acid, that may be present in the stomach fluid. It is also recently been discovered, that there may be a risk to health when too large a quantity of these products is ingested. In addition to the over the counter products, there are pharmaceutical products that can only be obtained with a physician's prescription. These prescription products are often used to reduce or prevent the pain associated with a gastric disturbance, esophagus reflux (heart burn); gastric ulcer and the like. As in the case of the over the counter antacid products, these prescription remedies must be taken with caution and in limited doses.

It has been found that there is a need for a method for treating stomach acidity whose active ingredient may be taken as often as a food. This desired method should be easily ingested and convenient in use. This desired method should begin to provide relief in a very short time after ingestion.

SUMMARY OF THE INVENTION

The present invention may be briefly described as: A method for treating excessive stomach acidity by ingesting a determined dose of milled, pulverized, or ground fava beans. This treatment may be taken prior to or after the onset of symptoms A first method for providing a predetermined dose is in the form of a chewable wafer that has a predetermined quantity of the milled, pulverized or ground fava beans as its main active ingredient.

A second method is for providing a predetermined dose of the milled, pulverized or ground fava beans in the form of a baked product such as a biscuit or cookie. A milled flour of the fava beans is its main active ingredient.

In addition to the above summary, the following disclosure is intended to be detailed to insure adequacy and aid in the understanding of the invention. However, this disclosure, describing embodiments of the invention, is not intended to describe each new inventive concept that may arise. These specific embodiments have been chosen to describe at least one preferred or best mode for the method of the present invention.

DETAILED DESCRIPTION OF THE INVENTION

The method of the present invention includes ingesting a predetermined dose of dried fava beans that have been milled, pulverized or ground into a fine powder, flour, meal or the like. In this application, the term fava bean flour is generally used to describe milled, pulverized or ground fava beans.

Fava beans grow as an annual type of the legume family. The fava bean is cultivated in a few varieties at small farms. In its large grain or large seed type, it can be supplied as fresh or dried. The fava bean is cultivated as a principal crop in the Sicily and Puglia Provinces of Southern Italy.

Surprisingly it has been discovered, that ingesting ground fava beans has relieved excess stomach acid. However, it is not fully understood how the milled or ground fava beans react interior of the stomach for providing the resultant relief from excess stomach acid.

In order to try to understand this antacid effect, laboratory tests have been conducted by the United States Testing Co., Hoboken N.J. The laboratory testing has shown that one gram of finely ground fava beans will neutralize 8.6 milligrams of hydrochloric acid.

One reference source describes the seeds of a fava bean, when dried as containing in media: water 13%; nitrogen substance 2.5%, fat 2%; extractive substance 50%; cellulose 7% and mineral salt (ash) 3%.

The predetermined dose of the ground fava beans may be ingested directly or mixed with a liquid. However ground fava bean flour is white-yellowish in color and may be described as sweet to the palate, yet sour of taste. Therefore direct ingestion of the flour alone may not be pleasing to some individuals.

A preferred method for delivering a dose of fava bean flour is in the form of a chewable wafer. Each wafer may include natural sweetening ingredients, such as dextrose, sugar, or the like, and flavorings such as chocolate, vanilla, coconut or the like. However, when needed, artificial sweeteners may be used. The wafer may be made by a method known as compression molding. For example, it has been found that wafers that weigh 4000 mg. and contain at least 2000 mg. of ground fava beans, has provided a satisfactory minimum dose. The ground fava bean acts as the active ingredient. However the wafer may include inactive ingredients, that are known as binders, in addition to the sweeteners and flavorings. The 4000 mg wafer is approximately 22 mm.×8 mm. thick (⅞ in.×¼ in.). A wafer or wafers of this size are convenient for carrying and for use as needed. It has been found that ingesting one wafer provides the desired relief from excess stomach acidity.

Another alternative method for delivering a dose of ground fava beans is in the from of a biscuit or cookie. It is preferred that the cookie or biscuit be made of fava bean flour, as its only flour. This provides a product that is gluten free. Allowing people who are gluten intolerant to ingest the cookie or biscuit. It has also been found that effective results are obtained when the quantity of fava bean flour is at least 60% by weight of the ingredients.

One typical recipe for making one kg. of a baked product is:

700 g. Fava Bean Flour; 25 g. Honey; 3 Eggs; 50 g. Milk, 100 g. Sugar; 25 G Ammoniac; 300 g. Water. The biscuits or cookies are formed to the desired size then baked at 200–220 degrees Celsius for 10 minutes.

It has been found that it is only necessary to ingest one small cookie to begin to feel relief. For severe cases of indigestion, it may take up to three cookies or biscuits to provide relief. This example is based on a cookie or biscuit that weighs approximately one ounce.

It is anticipated that the method of treating excessive stomach acid may include delivery of a dose of ground fava beans in other edible products such as caplets, flavored drink mixes, etc. The flour of fava beans may also be used to make food products generally known as pasta, for delivery of the desired dose. It has been found that a pasta made from a flour that has a composition of at least 60 percent fava bean flour, by weight, will provide the desired results.

As previously mentioned, the method of treatment of the present invention may be taken in anticipation of stomach acidity or after its occurrence.

It is recommended that a minimum dose of fava bean flour be at least 1000 mg., for providing relief from excessive stomach acidity.

What is claimed is:

1. A method of treating excess stomach acidity by ingesting a dose of at least 2000 mg of fava bean flour, wherein said dose is incorporated into at leas one molded 4000 mg chewable wafer and said fava bean flour is the main active ingredient for a reduction of the excess stomach acidity.

2. A method as recited in claim 1 wherein said wafer is compression molded.

3. A method as recited in claim 1 wherein said dose is incorporated into an edible product, and said fava bean flour being at least 60 percent, by weight, of the ingredients.

4. A method as recited in claim 1 wherein said dose is incorporated into a composition for an edible product, said fava bean flour being the only flour, and said fava bean flour being at least 60 percent, by weight, of the ingredients.

5. A method as recited in claim 1 wherein said dose is incorporated into a composition for consumption as a drink.

* * * * *